United States Patent [19]
Huber et al.

[11] Patent Number: 5,976,812
[45] Date of Patent: Nov. 2, 1999

[54] ACTIVATED AMPHETAMINES

[75] Inventors: Erasmus Huber, Finning; Christian Klein; Rudolf Vogel, both of Weilheim; Bruno Zink, Uffing; Wolfgang Rollinger, Polling, all of Germany

[73] Assignee: Roche Diagnostics GmbH, Mannheim-Waldhof, Germany

[21] Appl. No.: 08/896,330

[22] Filed: Jul. 17, 1997

[30] Foreign Application Priority Data

Jul. 25, 1996 [DE] Germany .............................. 196 30 102

[51] Int. Cl.$^6$ ...................... C07C 327/22; C07C 323/41; C07K 19/00; A61K 51/10
[52] U.S. Cl. .................... 435/7.1; 424/193.1; 424/178.1; 530/391.1; 530/391.7; 558/254; 560/24; 560/145; 564/192; 564/381
[58] Field of Search ...................... 560/24, 145; 558/254; 435/721; 424/193.1, 178.1; 530/391.1, 391.7

[56] References Cited

U.S. PATENT DOCUMENTS

| 4,329,281 | 5/1982 | Christenson et al. . | |
|---|---|---|---|
| 4,894,443 | 1/1990 | Greenfield | 530/388 |
| 5,002,883 | 3/1991 | Bieniarz et al. | 435/176 |
| 5,595,741 | 1/1997 | Huber et al. . | |

FOREIGN PATENT DOCUMENTS

| 0386644 | 3/1990 | European Pat. Off. . |
|---|---|---|
| 9015798 | 12/1990 | WIPO . |

*Primary Examiner*—Keith D. MacMillan
*Assistant Examiner*—T. Wessendorf

[57] ABSTRACT

The invention concerns activated amphetamine derivatives, a process for their production as well as their use for producing immunogens or detection conjugates carrying amphetamine groups. A further subject matter of the invention are new conjugates carrying amphetamine groups, a process for the production thereof as well as their use for the production of antibodies or for the determination of amphetamine or derivatives thereof.

22 Claims, 2 Drawing Sheets

ACTIVATED AMPHETAMINES

DESCRIPTION

The invention concerns activated amphetamine derivatives, a process for their production as well as their use for the production of immunogens or detection conjugates carrying amphetamine groups. The invention in addition concerns new conjugates carrying amphetamine groups, a process for their production as well as their use to produce antibodies or to determine amphetamine or derivatives thereof.

Amphetamine and related substances (for the sake of simplicity usually summarized under the term "amphetamines" in the following) belong to the group of psychoanaleptics and have a sympathomimetic action and addiction-promoting properties. They therefore have a large potential for abuse and in this connection there is a need for analytical determination and detection methods.

In particular immunological methods were developed in previous years to control drug abuse since these are rapid and cost-effective methods for detecting narcotics in body fluids. In order to produce antibodies which can be used suitably in such immunoassays it is necessary to produce an immunogen by coupling amphetamine to a suitable carrier, subsequently to produce antibodies in a known manner and to isolate these antibodies.

Conjugates of amphetamines and carrier substances are known from the state of the art. In a series of publications (1–9) conjugates of amphetamines with polypeptides or detection groups such as fluorescent dyes are described in which the coupling is achieved via a linker which is bound to the ethylamine side group of the amphetamine molecule. However, antibodies that are obtained after immunization with such an immunogen exhibit a high cross-reactivity with various amphetamine derivatives which differ in the substitution of the ethylamine side chain (22, 23). They are therefore of only limited suitability for analytics especially if it is necessary to differentiate between amphetamine, methamphetamine and ephedrine.

Furthermore the production of amphetamine-carrying conjugates is known from the state of the art in which the coupling is achieved by a substitution on the aromatic ring (10–21). However, when a substituent which has an activatable group is introduced on the aromatic ring system the amino function of the amphetamine side chain (primary amino group in the case of amphetamine, secondary in the case of methamphetamine) must be blocked during the activation by introducing a protective group before the conjugation step (11,21). After the conjugation is completed this group must be removed to restore the desired amphetamine epitope. The complete cleavage of the protective group cannot be detected especially when using a macromolecular carrier such as a polypeptide. Furthermore the function of the conjugate may be impaired (e.g. denaturation of a reporter enzyme) due to the reaction conditions required for the cleavage of the protective groups (as a rule large pH changes by an acid or a base or the action of strong oxidizing or reducing agents).

Aoki et al (13) describe an immunoassay for methamphetamine using a new antibody. The antibody was obtained after immunization with a conjugate which was prepared by a one-step process in which mercaptosuccinyl-BSA, p- or o-aminomethamphetamine and 4-(maleimidomethyl) cyclohexane-1-carboxylic acid succinimide ester (MCCS) were reacted. In this reaction the succinimide group can react with the amino group on the aromatic ring or/and with the amino group in the ethylamine side chain so that no specific product is obtained. The production of stable amphetamine derivatives which carry an activated linker function on the aromatic ring system is also not disclosed.

WO90/15798 discloses heterobifunctional reagents which are suitable for the production of hapten-peptide derivatives. These reagents are aminoalkylmaleimides, the linkage with the hapten being achieved by amidation of carboxyl groups. Phenobarbital, diphenylhydantoin, carbamazepine, valproic acid, thyroxine (T4), triiodothyronine (T3), oestrone, oestradiol, progesterone, testosterone, aldosterone, folic acid, methyltetrahydrofolic acid or cyanocobalamine (vitamin $B_{12}$) are mentioned for example as suitable haptens; however, amphetamines are not mentioned.

The object of the present invention is to provide activated amphetamine derivatives that are nevertheless stable and storable which enable these haptens to be coupled via the aromatic ring system to a conjugation partner without requiring an activation after the conjugation such as a cleavage of the protective group outside a pH range of 6.0 to 8.5 which may lead to a loss of biological activity.

The invention also concerns conjugates which are produced using the amphetamine derivatives according to the invention. Yet a further subject matter is a process for the production of the amphetamine derivative or the conjugate carrying the amphetamine according to the invention.

Yet a further subject matter is the use of a conjugate according to the invention in a process for obtaining antibodies directed towards amphetamines or for the determination of amphetamines.

The object of the invention is achieved by an activated amphetamine derivative characterized by the structural formula

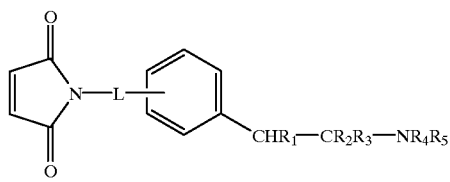

in which $R_1$ is H or OH, $R_2$, $R_3$, $R_4$ and $R_5$ are independently of one another H, $CH_3$ or $C_2H_5$, and L is a linker with a chain length of 4–30 atoms, or a salt thereof.

The linker chain contains optionally substituted C atoms and can contain heteroatoms such as N, O and S which can be substituted independently of one another. Examples of substituted atoms in the linker chain are —C($R_6$)$_2$—, —$NR_6$—, —$CR_6OR_6$— and —C(O)—, in which $R_6$ in each case independently of one another preferably denotes hydrogen or $C_1$ to $C_5$ alkyl. The linker can also contain multiple bonds i.e. two neighbouring atoms in the linker can be —$CR_6$=$CR_6$—, —C≡C— or —$CR_6$=N—.

L preferably has a chain length of 6 to 20, more preferably a length of 8 to 18 atoms.

In general linkers are used which are essentially unsubstituted and in one embodiment the atoms in the linker chain are selected independently of one another at each occurrence from —$CH_2$—, —CH=, —C≡, —NH—, =N—, —CHOH—, —C(O)—, —O— and —S—. In another embodiment no multiple bonds are present within the linear linker chain.

A major advantage of the activated amphetamine derivatives according to the invention is that it is not necessary to protect the amine group in the ethylamine side chain when they are later reacted with a suitable conjugation partner. As a result it is possible to ensure on the one hand that the amphetamine group is present in completely active form and on the other hand further process steps (protective group cleavage) are avoided which could have resulted in an impairment of the activity of the conjugate partner. The amphetamine derivatives according to the invention can therefore be used particularly advantageously when at least one of $R_4$ and $R_5$ is H.

The linker is preferably arranged in the p-position relative to the ethylamine side chain. A configuration in the o- or m-position is, however, also possible. The best results are achieved for those amphetamines in which the least possible influence on the accessibility of the amphetamine epitope is achieved by the spatial linkage of the linker with the particular amphetamine.

In a preferred embodiment L is $[-(CH_2)_o-NH-C(O)-]_p-(CH_2)_q-X-$, in which o at each occurrence is independently 2 to 6, p is 1 or 2, q is 2 to 10 and X is selected from O, NH and a bond. X is preferably a bond.

In the present invention activated amphetamine derivatives in which L has the structure $-(CH_2)_o-NH-C(O)-(CH_2)_q-$, wherein o and q have the meanings stated above, have turned out to be particularly suitable. In one embodiment o is 2 to 4, preferably 2 and q is 3 to 8, preferably 4 to 6.

The activated amphetamine derivatives according to the invention are suitable for use with the various amphetamines corresponding to the definition of the residues $R_1$ to $R_5$. In practice particularly important amphetamine derivatives are those in which $R_3$ and $R_5$ are each H i.e. the activated derivatives of for example amphetamine, methamphetamine, ephedrine, β-phenylethylamine and norphedrine. The activated derivatives of amphetamine and methamphetamine are of particular importance.

A further subject matter of the invention is a conjugate comprising at least one amphetamine group and a conjugation partner which is characterized in that it is obtainable by reacting the maleinimide group of an activated amphetamine derivative according to the invention with an SH group of the conjugation partner. $R_4$ as well as $R_5$ are preferably H.

The SH group of the conjugation partner can be a native (naturally occurring) SH group or/and have been produced by derivatization of the conjugation partner.

A further subject matter of the invention is a conjugate with the structural formula

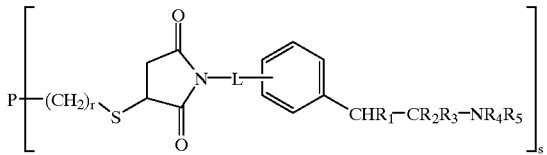

in which L is $[-(CH_2)_o-NH-C(O)-]_p-(CH_2)_q-$, o, p, q and $R_1$ to $R_5$ are defined as above, P is a conjugation partner, r is 0 to 10 and s is 1 to 40, or a salt thereof.

Preferred embodiments relating to the exact structure of the linker as well as the meaning of the residues $R_1$ to $R_5$ correspond to that stated above for the activated amphetamine derivative.

P can be a polypeptide such as for example a carrier or a detection polypeptide such as an immunoglobulin or an enzyme. If P is a carrier, an immunogen or a polyhapten is for example obtained by the conjugation. However, P can also be a label, selected for example from dyes, fluorescent or luminescent dyes, a metal label or other labels used in conventional detection methods.

In some applications for the conjugates according to the invention such as for example in immunoassays it may be preferable that the conjugation partner is bound to a solid phase or is capable of binding to a solid phase. Suitable methods for this are known to a person skilled in the art and are not elucidated in more detail. The ability to bind to a solid phase can be achieved by using suitable binding pairs such as for example biotin and avidin/streptavidin.

A further subject matter of the invention is a process for the production of an activated amphetamine derivative which is characterized in that a linker which is suitable for reaction with maleinimido-alkylamine is introduced on the aromatic ring of the amphetamine in a one-step or multiple step synthesis, wherein the amine group of the amphetamine ethylamine side chain is protected during the synthesis, the derivative that is formed is reacted with maleinimido-alkylamine, the protective group is removed and the activated amphetamine derivative is isolated.

In this process the amphetamine ethylamine side chain is protected by the usual protective groups and it is obvious that the protective groups only have to be present during synthesis steps in which a reaction of the amine group occurs or is to be expected. After the isolation of the activated amphetamine derivative, the completeness of the protective group cleavage can be checked and the isolated material can be optionally further purified in order to obtain a product which is essentially free of protective groups.

The suitable group for reaction with maleinimidoalkylamine is preferably an N-hydroxysuccinimide ester. The production of linkers which contain an N-hydroxysuccinimide ester group is basically known from the state of the art. Further embodiments are explicitly stated in the examples of this invention and specific structural examples of such N-hydroxysuccinimide esters are shown in the attached Figures (compound 7 and 16).

Yet a further subject matter of the present invention is a process for the production of a conjugate which is characterized in that an activated amphetamine derivative as defined above is reacted together with a reagent $P-[-(CH_2)_r-SH]_s$ in which P, r and s are defined as above under such conditions that an addition of the SH groups to the double bond occurs in the maleinimido functionality and the reaction product is isolated.

The advantage of conjugates according to the invention prepared in this manner compared to conventionally used conjugates is that after the conjugation step it is not necessary to leave the protective group which can lead to an inactivation of the conjugate partner. Furthermore it is possible to ensure that the protective groups are completely removed by means of the analytical methods that are available. As a result it is ensured that the amphetamine group is quantitatively available for subsequent applications.

In addition the invention concerns the use of a conjugate according to the invention in a process for the production of antibodies directed towards amphetamines as well as for the determination of amphetamines.

Antibodies are produced by immunizing an experimental animal with the immunogen i.e. a conjugate according to the invention in which case the conjugation partner is a carrier.

The immunization is carried out in a conventional manner known to a person skilled in the art, the immunogen is preferably administered to the experimental animal in combination with an adjuvant. It is particularly preferable to use Freund's adjuvant as the adjuvant or aluminium hydroxide together with Bordetella pertussis. The immunization is preferably carried out for several months with at least four immunizations at intervals of 4 to 6 weeks. The immunogen is preferably injected intraperitoneally.

Polyclonal antibodies are obtained from animals immunized in this manner which are purified by conventional isolation and processing methods. Alternatively in order to produce monoclonal antibodies B lymphocytes can also be isolated which are fused with a permanent myeloma cell line according to the known method of Köhler and Milstein (Nature 256 (1975), 495–497). The primary cultures of hybrid cells that are formed in this process are cloned in the usual manner for example by using a commercial cell sorter or by "limited dilution" and cultures which react positively towards an amphetamine in a suitable test procedure are processed further.

Antibodies obtained in this manner are used advantageously in immunoassays. In particular such antibodies are used bound to a label or present on a solid phase i.e. bound to a solid phase or capable of binding to a solid phase.

The immunoassay is preferably carried out in the form of a heterogeneous immunoassay particularly preferably on a chromatographic test strip as described for example in DE-OS-44 39 429 or DE-OS-40 24 919.

Such a test strip preferably contains absorptive zones arranged one behind the other on a carrier foil: an analyte application zone, a conjugate zone on which a labelled binding partner and optionally a binding partner with a specific binding site (e.g. biotin) for the subsequent capture zone are accommodated, a capture zone on which a capture reagent for the analyte or an analyte antibody or a specific capture reagent for a specific binding site of a binding partner (e.g. streptavidin) is applied and a target zone in which the label that is not captured is measured.

If the immunoassay is carried out according to a sandwich principle, a complex of analyte and a labelled antibody forms in the conjugate zone after applying the analyte to the application zone which is immobilized there via a further antibody which is either solid phase bound in the solid phase zone or can be bound there via a specific binding pair e.g. biotin-streptavidin.

The immunoassay is preferably carried out according to an IEMA test principle (immuno enzymetric assay). The test procedure is preferably carried out in an immunological reaction cell which comprises a conjugate zone and a capture zone. A detection reagent is present in the conjugate zone e.g. a labelled antibody which is preferably in excess compared to the analyte to be determined. Excess labelled antibodies are captured in the capture zone by analyte analogues such as solid phase bound polyhaptens whereas labelled analyte-antibody complexes are detected in the flow of the reaction cell. In this case there is an ascending calibration curve i.e. the measured signal increases with the analyte concentration.

A further subject matter of the invention is a reagent kit which comprises an amphetamine derivative or/and a conjugate according to the invention. Such a reagent kit can in the simplest case only comprise an activated amphetamine derivative in order to enable a user to produce specific conjugates for his particular application purpose. The kit can additionally or alternatively already contain ready-made conjugates which can be used in immunizations or determination methods for amphetamines. Furthermore the kit can also contain common auxiliary substances, buffer substances and additives and optionally anti-amphetamine antibodies. A preferred reagent kit is the chromatographic test strip described above.

The invention is described in more detail by the following examples in conjunction with the attached figures in which

EXAMPLES

Example 1

Figure 1:
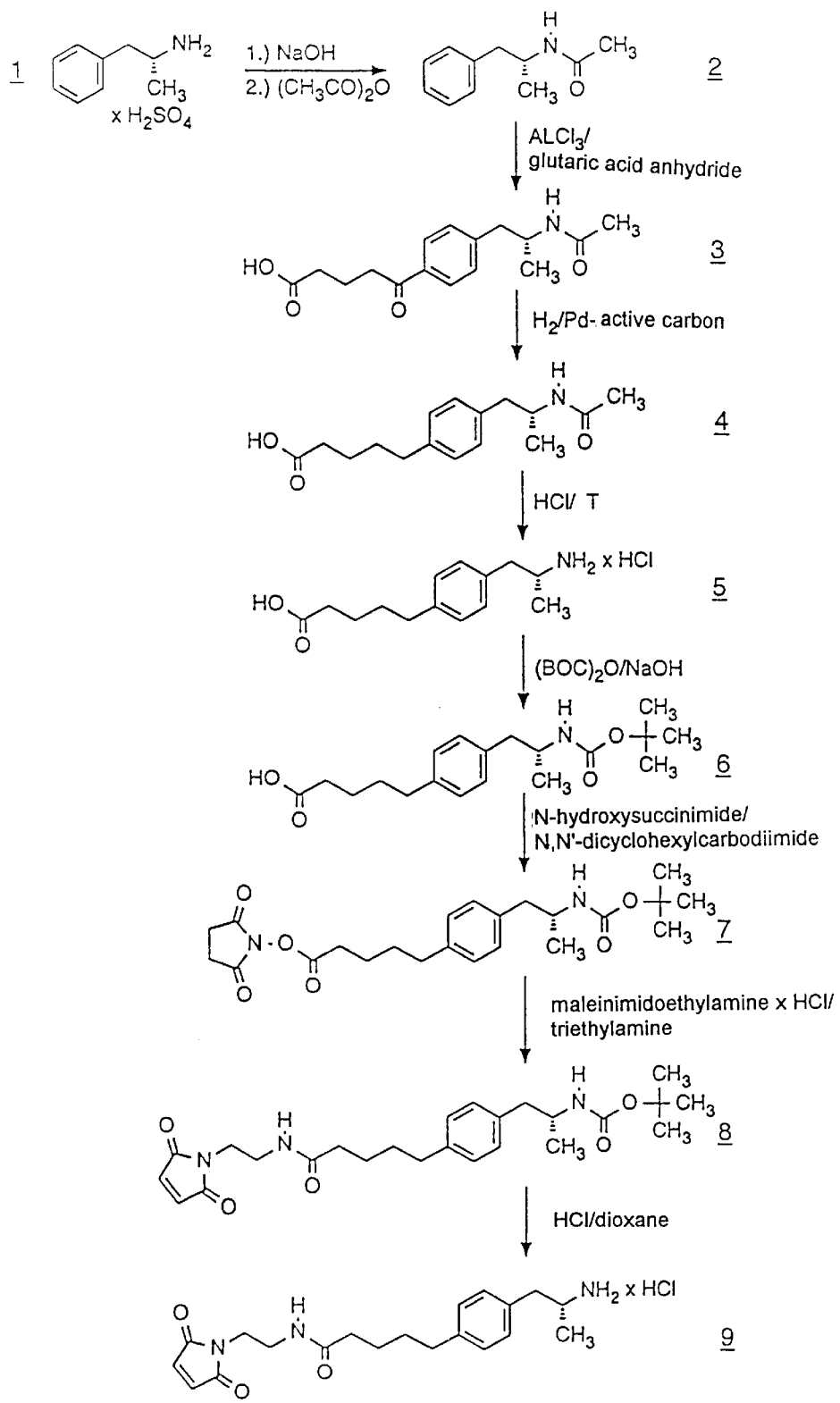
FIG. 1 show the synthetic scheme for amphetamine-p-carboxybutylmaleinimidoethylamide and FIG. 2 shows the synthetic scheme for methamphetamine-p-carboxybutylmaleinimidoethylamide.
Figure 2:
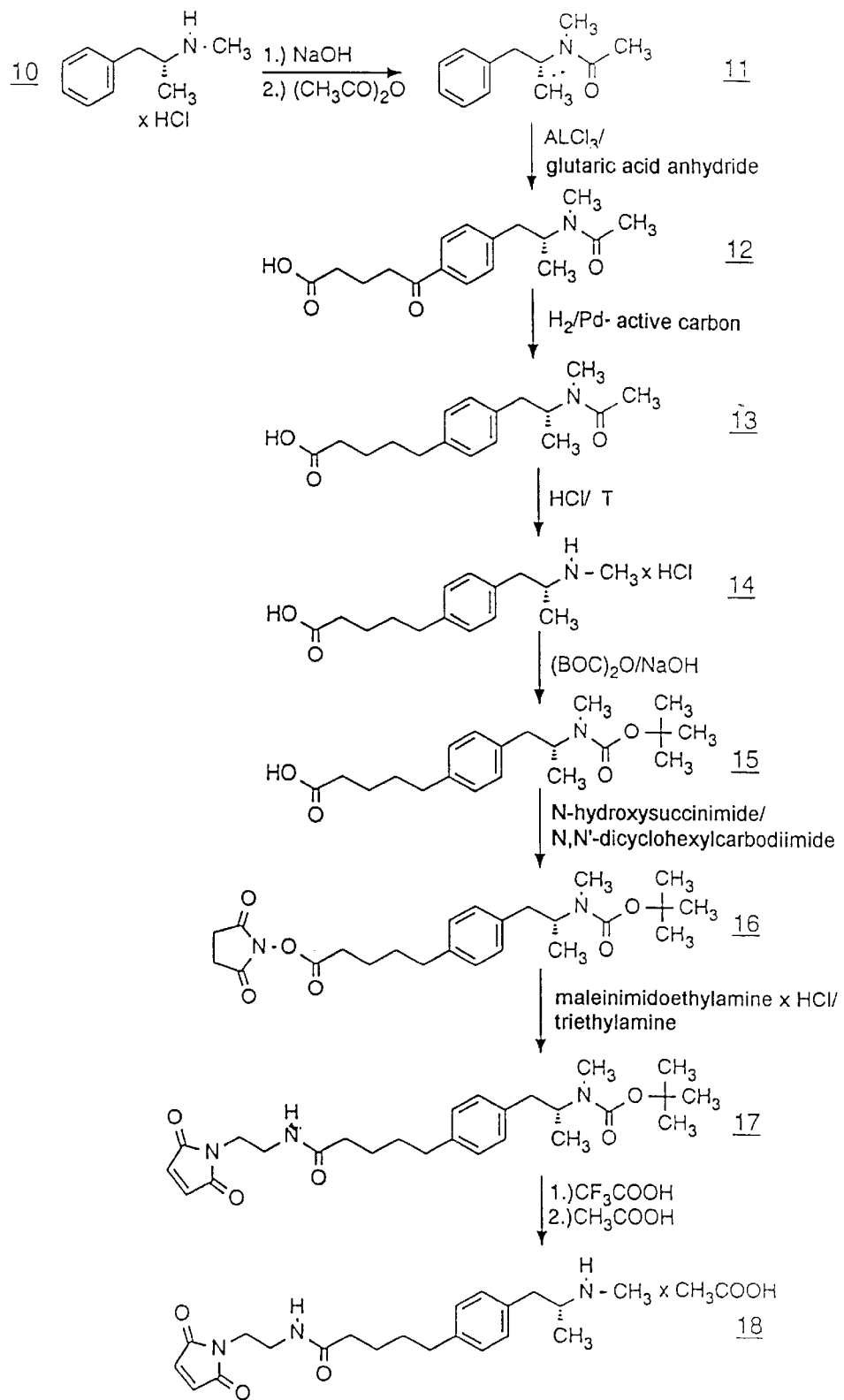

Production of amphetamine-p-CB-MEA (amphetamine-p-carboxybutyl-maleinimidoethylamide) (hydrochloride)

1. (S)-N-(1-Methyl-2-phenylethyl)acetamide(N-acetyl-d-amphetamine) 2

23.3 g (0.1 mol) dexamphetamine sulfate is suspended in 75 ml water and admixed at room temperature with a solution of 10 g (0.25 mol) NaOH in 100 ml water. After a brief vigorous shaking an oil separates out which is extracted with 3×100 ml toluene. The extract is dried with 50 g $K_2CO_3$. Subsequently it is filtered through a fluted filter.

50 ml (0.5 mol) acetic anhydride is added to the filtrate and the solution is heated for 1.5 h under reflux. Subsequently it is concentrated in a water jet vacuum at 55° C. bath temperature and the crystalline residue is dried for ca. 1 h in a high vacuum. The product is digested for 1–2 h with 150 ml diisopropyl ether, suction filtered and dried for 12–14 h in a vacuum-drying cabinet (ca. 150 mbar) at 40° C.

Yield: 19.1 g (17.7 g of theory) of a colourless solid containing a slight amount of acetic acid.

TLC: silica gel 60; ethyl acetate/methanol 1/1 (v/v); $R_f$=0.86.

2. N-Acetyl-p-carboxypropylcarbonyl-d-amphetamine 3

The entire amount of amide 2 (0.1 mol) obtained under 1) is dissolved together with 17.1 g (0.15 mol) glutaric acid anhydride in 500 ml methylene chloride freshly distilled over $Al_2O_3$, the solution is cooled to 0–5° C. Within 30 min 53.4 g (0.4 mol) $AlCl_3$ is added in portions to the solution while shaking vigorously and continuously cooling the flask to 0–5° C. It is stirred for a further 4 hours while cooling, then the mixture is allowed to reach room temperature with continuous further stirring and allowed to stand overnight. The partially lumpy brown-yellow flask contents are cooled again to 0–5° C. and admixed with 200 ml 3 M HCl while stirring during which the large particles slowly dissolve within 1 h and a red oil separates out. The methylene chloride phase at the bottom of the flask is withdrawn with a pipette and 250 ml fresh methylene chloride is added. It is allowed to stir for a further 15 min, then the organic solvent is again removed and combined with the first amount of methylene chloride. The organic phase is extracted with 250 ml water in a separating funnel. Subsequently the aqueous extract is combined with the oily residue that still remains in the reaction flask. 1 n NaOH is slowly added to the mixture while stirring at room temperature until the aqueous phase exhibits a weak alkaline reaction (pH 8–9). It is allowed to stir further (decomposition of organic acid chloride that forms) during which the pH value is kept at about 8–9 by adding NaOH again. The mixture remains standing overnight at RT. Subsequently it is adjusted to pH 4–5 with 3 n HCl and 200 ml dioxane is added during which a solid homogeneous solution forms. This is extracted with 3×200 ml ethyl acetate. The extract is dried with ca. 80 g Na$_2$SO$_4$ and evaporated to dryness on a rotary evaporator.

The oily brown residue is dissolved in the smallest possible amount of ethyl acetate/methanol 4/1 (v/v) and applied to a column (8.5×60 cm, silica gel, Merck Co.). It is eluted with ethyl acetate/methanol 4/1 (v/v) and the individual fractions (100 ml) are tested by means of TLC and silica gel 60, F$_{254}$ (same mobile solvent). The fractions containing the pure product are pooled and the solvent is removed on a rotary evaporator. The residue is recrystallized from 80 ml water/isopropanol 6/1 (v/v), suction filtered and dried for 12–14 h in a vacuum-drying cabinet (ca. 150 mbar) at 40° C.

Yield: 8.4 g (28.9% of theory) pale yellow crystals.

TLC: silica gel 60; ethyl acetate/methanol 4/1 (v/v); R$_f$=0.60.

3. N-Acetyl-p-carboxybutyl-d-amphetamine 4

7.28 g (25 mmol) of the phenylketone 3 is dissolved in 100 ml anhydrous and peroxide-free THF and 0.5 g fresh Pd/active carbon is added. Subsequently it is hydrogenated in a glass apparatus (shaking duck) at a slight overpressure (40–50 mbar) and RT.

Reaction period: 1 h

Theoret. H$_2$ uptake: 1.12 l; pract. H$_2$ uptake: ca. 1.2 l

Subsequently the apparatus is aerated with N$_2$ and abundantly flushed to drive out residual hydrogen. The catalyst is removed by filtration, but remains wetted with solvent and is subsequently disposed of.

The solution is evaporated on a rotary evaporator and dried for 12–14 h in a vacuum-drying cabinet (ca. 150 mbar) at 40° C. The product is used for the next step without further purification.

Yield: 6.95 g (theory: 6.93 g) colourless solid.

TLC: silica gel 60; ethyl acetate/glacial acetic acid 9/1; R$_f$=0.70.

4. p-Carboxybutyl-d-amphetamine hydrochloride 5

6.93 g (25 mmol) of the acetamide 4 is stirred for 30 h under reflux in 100 ml conc. HCl. Afterwards it is allowed to slowly cool to RT and allowed to stand overnight. The precipitated product is suction filtered, digested with 100 ml acetone, again suction filtered and dried for 12–14 h in a vacuum-drying cabinet (ca. 150 mbar) at 40° C.

Yield: 4.55 g (67% of theory) colourless solid.

TLC: silica gel 60; ethyl acetate/glacial acetic acid 9/1 (v/v); R$_f$=0.08.

5. N-BOC-p-Carboxybutyl-d-amphetamine 6

4.07 g (15 mmol) of the hydrochloride 5 is dissolved in 120 ml dioxane/water 2/1 (v/v) and admixed with 22.5 ml 2 n NaOH (45 mmol). 3.6 g (16.5 mmol) di(tert.-butyl) dicarbonate (BOC$_2$O) in 20 ml dioxane is added and it is stirred for 2 h at RT. Salt that may have precipitated is dissolved again by adding up to 30 ml water. The pH value is checked and if necessary adjusted to 9.0–9.2 with 2 n NaOH. Then a further 0.5 g BOC$_2$O is added and it is again allowed to stir for a further 2 h at the same temperature. Subsequently it is adjusted to pH 2.0 with 2 m KHSO$_4$ solution, diluted with 200 ml water and the carboxylic acid 6 is extracted with 2×200 ml ethyl acetate. The extract is washed with 200 ml water, dried with 30 g Na$_2$SO$_4$ and the solvent is evaporated on a rotary evaporator.

The remaining oil is dried for 2 h at 40° C. in a high vacuum (rotary evaporator).

Yield: 5.09 g (theory: 5.03 g) viscous, slightly brown oil.

TLC: silica gel 60; ethyl acetate/glacial acetic acid 9/1 (v/v); R$_f$=0.86.

6. N-BOC-d-Amphetamine-p-carboxybutyl-N-hydroxysuccinimide ester 7

4.02 g (12 mmol) of the free carboxylic acid 6 is dissolved in 60 ml anhydrous THF and admixed with 1.66 g (14.4 mmol) N-hydroxysuccinimide and 2.97 g (14.4 mmol) N,N'-dicyclohexylcarbodiimide. It is allowed to stir for 18 h at RT during which colourless crystals of N,N'-dicyclohexylurea sediment. These are subsequently removed by filtration, the filtrate is evaporated in a rotary evaporator and the residue is dissolved in 50 ml ethyl acetate during which urea in turn remains as a sediment. After filtering again the organic solvent is washed with 2×50 ml water, dried with ca. 5 g Na$_2$SO$_4$ and evaporated. The residue is digested with diisopropyl ether in a closed flask until crystallization is completed, suction filtered and dried for 12–14 h in a vacuum-drying cabinet (ca. 150 mbar) at 40° C. For a longer storage an additional drying in a desiccator over P$_2$O$_5$ is recommended.

Yield: 3.31 g (64% of theory) colourless, fine-crystalline solid.

TLC: silica gel RP-18; nitromethane/ethanol 9/1 (v/v); R$_f$=0.72.

7. N-BOC-d-Amphetamine-p-carboxybutyl-maleinimidoethylamide 8

3.24 g (7.5 mmol) of the active ester 7 is dissolved in 50 ml freshly distilled DMF and admixed with 1.32 g (7.5 mmol) maleinimidoethylamine hydrochloride (MEA×HCl) and 2.25 ml triethylamine. It is allowed to stir for 1.5 h at RT, then a further 0.27 g MEA×HCl is again added. During the course of the reaction a precipitate of triethylammonium hydrochloride forms. After stirring for a further 2 h at RT the solvent is removed on a rotary evaporator (oil pump vacuum, bath temperature: 45° C.), the residue is digested for ca. 30 min with ca. 20 ml 5% acetic acid. The solid is suction filtered, taken up in 100 ml ethyl acetate and washed with 50 ml water. The organic phase is dried with ca. 5 g Na$_2$SO$_4$ and the solution is evaporated on a rotary evaporator (water-jet vacuum). 2.5 g crude product is obtained in this way which is purified by chromatography on a silica column (silica gel 60, 3.8×40 cm; ethyl acetate/glacial acetic acid 99/1 (v/v)). The fractions containing the pure product are pooled, concentrated on a rotary evaporator and the residue is digested for ca. 1 h with ca. 30 ml diisopropyl ether. It is suction filtered and dried for 12–14 h in a vacuum-drying cabinet (ca. 150 mbar) at 40° C.

Yield: 1.76 g (51% of theory) colourless solid.

TLC: silica gel 60; ethyl acetate/glacial acetic acid 99/1 (v/v); R$_f$=0.47 Detection by spraying with ninhydrin solution (Merck Co.) or KMnO$_4$ solution (0.1%).

8. d-Amphetamine-p-carboxybutyl-maleinimidoethylamide hydrochloride (AH, amphet-p-CB-MEA hydrochloride) 9

1.57 g (4 mmol) of the BOC-protected maleinimido compound 8 is dissolved in 25 ml 2 m HCl in dioxane (freshly prepared) and allowed to stand for 30 min at RT without stirring. The precipitated oil is digested for 1 h with 20 ml ethyl acetate during which complete crystallization occurs. The product is suction filtered and dried for 48 h in a vacuum-drying cabinet (ca. 150 mbar) at 40° C.

Yield: 1.38 g (88% of theory) colourless solid.

TLC: silica gel 60; n-butanol/glacial acetic acid/water 50/15/25 (v/v/v); $R_f$=0.56 Detection by spraying with ninhydrin solution. (Merck Co) or $KMnO_4$ solution (0.1%).

HPLC:
column: Vydac C18/300 Å/5 µm/4.6×250 mm
precolumn: Nova-Pak C18/Guard-Pak
det.Wavelength: 225 nm
eluant:
  A: millipore water/0.1% TFA
  B: acetonitrile/0.1% TFA
gradient: 0–80% B in 0–40 min
sample amount: 20 µl (c=1 mg/ml)
flow: 1 ml/min
$t_r$: 16.3 min (impurities at 16.1 and 17.7 min)
Target content by HPLC: >90%

NMR ($d_6$DMSO): δ (ppm)=1.11 (d, J=6 Hz; 3H); 1.47 (m; 4H); 1.99 (m; 2H); 2.60–3.55 (m; 9H); 6.97 (s; 2H, —CH=CH—/important signal!); 7.14 (s, br; 4H); 7.92 (tr, s.br; 1H); signal —$NH_3^+$ variable (!).

Example 2

Methamphet-p-CB-MEA (methamphetamine-p-carboxybutylmaleinimidoethyl amide (acetate)

1. (S)-N-(1-N-Dimethyl-2-phenylethyl)acetamide (N-acetyl-d-methamphetamine) 11

18.6 g (0.1 mol) methamphetamine-hydrochloride is dissolved in 75 ml water and admixed at RT with a solution of 5 g (0.25 mol) NaOH in 100 ml water. After shaking vigorously for a short time, an oil separates which is extracted 3 times with 3×50 ml toluene. The extract is dried with 50 g $Na_2SO_4$ (shaking vigorously for ca. 1–2 min) and subsequently filtered over a fluted filter.

75 ml (0.5 mol) acetic anhydride is added to the filtrate and the solution is heated for 1.5 h under reflux. Afterwards it is evaporated in a water-jet vacuum at 55° C. bath temperature and dissolved in 200 ml ethyl acetate. The organic phase is washed in a separating funnel with 200 ml 1% $NaHCO_3$ and subsequently with 200 ml water. The solvent is removed by evaporation on a rotary evaporator and the oily crude product is dried for ca. 1 h at 40° C. in a high vacuum (rotary evaporator).

Yield: 18.1 g (95% of theory) pale brown oil containing a slight amount of acetic acid.

TLC: silica gel 60; ethyl acetate; $R_f$=0.41.

2. N-Acetyl-p-carboxypropylcarbonyl-d-methamphetamine 12

The entire amount of the amide 11 (95 mmol) obtained under 1.) is dissolved together with 16.26 g (143.5 mmol) glutaric acid anhydride in 475 ml methylene chloride freshly distilled over $Al_2O_3$, the solution is cooled to 0–5° C. Within 30 min 50.4 g (0.37 mol) $AlCl_3$ is added in portions to the solution while shaking vigorously and continuously cooling the flask to 0–5° C. It is stirred for a further 4 hours while cooling then the mixture is allowed to reach room temperature with continuous further stirring and allowed to stand overnight. The partially lumpy brown-yellow flask contents are cooled again to 0–5° C. and admixed with 225 ml 3 M HCl while stirring during which the large particles slowly dissolve within 1 h and a red oil separates out. The methylene chloride phase at the bottom of the flask is aspirated with a pipette and 280 ml fresh methylene chloride is added. It is allowed to stir for a further 15 min, then the organic solvent is again removed and combined with the first amount of methylene chloride. The organic phase is extracted with 250 ml water in a separating funnel. Subsequently the aqueous extract is combined with the oily residue that still remains in the reaction flask and stirred for 4 h at RT. Subsequently 200 ml dioxane is added during which an almost homogenous solution forms. This is extracted with 3×200 ml ethyl acetate. The extract is dried with ca. 80 g $Na_2SO_4$ and evaporated on a rotary evaporator.

The oily brown residue is dissolved in the smallest possible amount of ethyl acetate/methanol 4/1 (v/v)+1% glacial acetic acid and applied to a column (8.5×60 cm, silica gel 60, Merck Co.). It is eluted with ethyl acetate/methanol 4/1 (v/v)+1% glacial acetic acid and the individual fractions (100 ml) are tested by means of TLC on silica gel 60, $F_{254}$ (same mobile solvent). The fractions containing the pure product are pooled and the solvent is removed on a rotary evaporator. The residue is dissolved in 200 ml ethyl acetate and washed twice with 50 ml water each time. The organic solution is dried with ca. 10 g anhydrous $Na_2SO_4$ and the solvent is removed on a rotary evaporator.

Yield: 6.68 g (23% of theory) yellowish solid.

TLC: silica gel 60; ethyl acetate/methanol 4/1 (v/v); +1% glacial acetic acid; $R_f$=0.60.

3. N-Acetyl-p-carboxybutyl-d-amphetamine 13

6.68 g (21.9 mmol) of the phenylketone 12 is dissolved in 90 ml anhydrous and peroxide-free THF and 0.5 g fresh Pd/active carbon is added. Subsequently it is hydrogenated in a glass apparatus (shaking duck) at a slight overpressure (40–50 mbar) and RT. The hydrogenation comes to a standstill after about 1 h (1/3 of the theoretical $H_2$ volume is taken up) after which 0.5 g catalyst is again added. Strong $H_2$ uptake takes place and the hydrogenation is allowed to proceed to standstill (1–2 h).

Theoret.: $H_2$ uptake: 0.79 l; pract. $H_2$ uptake: ca. 081 l

Subsequently the apparatus is aerated with $N_2$ and abundantly flushed in order to drive out residual hydrogen. The catalyst is removed by filtration, but remains wetted with solvent in and is subsequently disposed of.

The solution is evaporated on a rotary evaporator and the remaining oil is subsequently dried in a high vacuum (rotary evaporator, water bath 40° C.). The product is used for the next step without further purification.

Yield: 7.03 g (theory: 6.37 g) colourless oil.

TLC: silica gel 60; ethyl acetate/glacial acetic acid 9/1 (v/v); $R_f$=0.56.

4. p-Carboxybutyl-d-methamphetamine hydrochloride 14

The entire amount (7.03 g) and 6.37 g (21.9 mmol) of the acetamide 13 obtained above is stirred for 48 h under reflux in 100 ml conc. HCl. Afterwards it is evaporated on a rotary evaporator and the oily residue is taken up in 100 ml water. The water phase is extracted with 2×30 ml ethyl acetate, the extract is dried with 5 g $Na_2SO_4$ and evaporated. It essentially contains non-saponified acetyl compound which if required can be used in a further saponification experiment. The water phase obtained above is treated with 1 g active charcoal, afterwards filtered, lyophilized and the lyophilisate (ca. 3 g) is digested with 2×100 diethyl ether for 30 min each time. The solid product is suction filtered and dried for 12–14 h in a vacuum-drying cabinet (ca. 150 mbar) at 40° C.

Yield: 2.90 g (46% of theory) slightly yellowish brown solid.

TLC: silica gel 60; n-butanol/glacial acetic acid/water 40/10/50 (v/v/v); $R_f$=0.39 (slight impurities at $R_f$=0.26 and 0.44 can be tolerated).

5. N-BOC-p-Carboxybutyl-d-methamphetamine 15

2.90 g (10 mmol) of the hydrochloride 14 is dissolved in 80 ml dioxane/water 1/1 (v/v) and admixed with 15 ml 2 n NaOH (18 mmol). 2.65 g (12 mmol) di(tert.-butyl) dicarbonate ($BOC_2O$) in 10 ml dioxane is added and it is stirred for 2 h at RT. Subsequently it is adjusted to pH 2.0 with 2 m $KHSO_4$ solution, diluted with 150 ml water and the carboxylic acid 6 is extracted with 2×100 ml ethyl acetate. The extract is dried with 10 g $Na_2SO_4$ and the solvent is evaporated on a rotary evaporator. The remaining oil is dried for 2 h at 40° C. in a high vacuum (rotary evaporator).

Yield: 3.40 g (97% of theory) viscous, almost colourless oil.

TLC: silica gel 60; ethyl acetate/glacial acetic acid 9/1 (v/v); $R_f$=0.90.

6. N-BOC-d-Methamphetamine-p-carboxybutyl-N-hydroxysuccinimide ester 16

3.36 g (10 mmol) of the free carboxylic acid 15 is dissolved in 50 ml anhydrous THF and admixed with 1.38 g (12 mmol) N-hydroxysuccinimide and 2.47 g (12 mmol) N,N'-dicyclohexylcarbodiimide. It is allowed to stir for 18 h at RT during which clear crystals of N,N'-dicyclohexylurea sediment. These are subsequently removed by filtration, the filtrate is evaporated on a rotary evaporator and the residue is dissolved in 70 ml ethyl acetate during which urea in turn remains as a sediment. After filtering again the organic solvent is washed with 2×30 ml water, dried with ca. 3 g $Na_2SO_4$ and evaporated. The residue is digested for 1 h with 50 ml petroleum ether in a closed flask, the solvent is decanted and the remaining oil is dried for at least 2 h at 40° C. in a high vacuum (rotary evaporator). For a storage over several days a storage temperature of $\leq -20°$ C. is recommended.

Yield: 4.02 g (91% of theory) viscous almost colourless oil.

TLC: silica gel RP-18; nitromethane/ethanol 9/1 (v/v); $R_f$=0.75.

7. N-BOC-d-Methamphetamine-p-carboxybutyl-maleinimidoethylamide 17

4.02 g (9 mmol) of the active ester 16 is dissolved in 70 ml freshly distilled DMF and admixed with 1.75 g (9.9 mmol) maleinimidoethylamine hydrochloride (MEA×HCl) and 3.0 ml triethylamine. It is allowed to stir for 1.5 h at RT, then a further 0.35 g MEA×HCl is again added. During the course of the reaction a precipitate of triethylammonium hydrochloride forms. After stirring for a further 2 h at RT the solvent is removed on a rotary evaporator (oil pump vacuum, bath temperature: 45° C.), the residue is taken up in 50 ml ethyl acetate and the organic phase is washed with ca. 50 ml 5% acetic acid and subsequently with 50 ml water. The organic phase is dried with ca. 5 g $Na_2SO_4$ and the solution is evaporated on a rotary evaporator (water-jet vacuum). Ca. 4.2 g crude product is obtained in this way which is purified by chromatography on a silica column (silica gel 60, 5.5×47 cm; ethyl acetate/glacial acetic acid 99/1 (v/v)). The fractions containing the pure product are pooled and concentrated on a rotary evaporator. The oily product is dried for ca. 2 h at 40° C. in a high vacuum (rotary evaporator).

Yield: 2.77 g (65% of theory) viscous, almost colourless oil.

TLC: silica gel 60; ethyl acetate/glacial acetic acid 99/1 (v/v); $R_f$=0.49 Detection by spraying with ninhydrin solution (Merck Co.) or $KMnO_4$ solution (0.1%) and by fluorescence quenching at $\lambda$=254 nm.

8. d-Methamphetamine-p-carboxybutyl-maleinimidoethylamide acetate 18

2.77 g (5.9 mmol) of the BOC-protected maleinimido compound 17 is dissolved in 45 ml 2 m HCl in dioxane (freshly prepared) and allowed to stand for 30 min at RT without stirring. The precipitated product (hydrochloride) is suction filtered on a nutsch filter and the crude product is purified by column chromatography (silica gel 60, 3.8×40 cm; ethyl acetate/glacial acetic acid/water 60/30/10 (v/v/v)) during which it is resalted to form the acetate. The fractions containing the crude product are pooled and concentrated on a rotary evaporator to a residual volume of 5–10 ml. It is diluted with water to a final volume of ca. 100 ml, the precipitated product is suction filtered and lyophilized. Subsequently the finished product is dried for 48 h in a vacuum-drying cabinet (ca. 150 mbar) at 40° C.

Yield: 1.85 g (77% of theory) colourless solid (without column chromatography).

TLC: silica gel; ethyl acetate/glacial acetic acid/water 60/30/10 (v/v/v); $R_f$=0.39 Detection by spraying with ninhydrin solution. (Merck Co) or $KMnO_4$ solution (0.1%).

HPLC:
  column: Vydac C18/300 Å/5 µm/4.6×250 mm
  precolumn: Nova-Pak C18/Guard-Pak
  det.Wavelength: 225 nm
  eluant:
    A: millipore water/0.1% TFA
    B: acetonitrile/0.1% TFA
  gradient: 0–80% B in 0–40 min
  sample amount: 20 µl (c=1 mg/ml)
  flow: 1 ml/min
  $t_r$: 17.0 min (impurities at 15.9 and 18.1 min)
  Target content by HPLC: >90%
  NMR ($d_6$DMSO): δ (ppm)=0.95 (d, J=6 Hz; 3H); 1.45 (m; 4H); 1.80 (s; 3H); 1.98 (m; 2H); 2.36 (s; 3H); 2.40–3.50 (m; 9H); 6.96 (s; 2H, —CH═CH—/important signal!); 7.09 (s, br; 4H); 7.89 (tr, s.br; 1H); signal —$NH_3^+$ variable (!).

At a slightly higher content of acetic acid the integral of the signal at δ(ppm)=1.80 can also correspond to up to 4.5 H (>5 H is not allowed since in this case the content of acetic acid is too high!).

Example 3

Immunization and production of antisera

Immunogens are produced by coupling the activated amphetamine derivative 9 according to example 1 or the activated methamphetamine derivative 18 according to example 2 to keyhole-limpet hemocyanin (KLH).

This coupling is carried out as follows:

Dissolve 250 mg KLH-lyophilisate (150 mg active substance=$5$–$10^{-5}$ mol) in 20 ml 0.1 M potassium phosphate buffer pH 7.0, add dropwise a solution of 24.5 mg (0.1 mmol) N-succinimidyl-S-acetylthiopropionate (SATP) in 3 ml dioxane and stir for 3 h at room temperature. Subsequently centrifuge. Apply the grey slightly opalescent supernatant to an AcA 202 column (∅=5 cm; l=25 cm; in 0.1 M potassium phosphate buffer pH 7.0) and elute with 0.1 M potassium phosphate buffer pH 7.0 (detection with a flow photometer at 226 nm and flat bed recorder).

Yield: 130 mg KLH-(S)ATP ($4$–$10^{-5}$ mmol); $\eta=3.54$ mg/ml; determined with a BCA test; BCA protein assay reagent (Pierce; order No. 23225X).

The solution obtained of KLH-(S)-ATP is admixed with 1.8 ml 1 M $NH_2OH$ solution and stirred for 1 h at room temperature. Subsequently a solution of 12 mg maleinimido compound in 3 ml DMSO is added and it is stirred for 16 h at room temperature. The mixture is centrifuged. The grey, slightly opalescent supernatant is applied to an AcA 202 column ($\emptyset=5$ cm; $l=25$ cm in 0.1 M potassium phosphate buffer pH 7.0) and eluted with 0.1 M potassium phosphate buffer pH 7.0 (detection with a flow photometer at 226 nm and flat bed recorder). Add 6 ml glycerol after the protein determination.

Yield: 90 mg immunogen; $\eta=1.33$ mg/ml (determined with the BCA test).

In each case 5 sheep are immunized with the immunogens obtained in this manner in Freund's adjuvant. The dose is 500 $\mu$g per animal. The immunizations are repeated over a period of 6 months or longer in each case at intervals of 4 weeks.

Antiserum samples are taken once monthly from all animals and examined for the presence of anti-amphetamine or anti-methamphetamine antibodies. The procedure for this measurement is described in example 4. For further examinations those antisera are selected which yield an adequately high measurement signal (at least 100 mA after 30 to 60 minutes colour development) at dilutions of 1:10,000 or higher. Three months after the start of the immunization the sera of all animals exhibited an adequately high signal.

Example 4

Detection of anti-amphetamine and anti-methamphetamine antibodies

Solutions Used coating buffer: 50 mM sodium bicarbonate; 0.09% sodium azide; pH 9.6 incubation buffer: 10 mM sodium phosphate; 0.1% Tween 20 (Brenntag Co.) 0.9% NaCl; 1% crotein C (CRODA GmbH Co.); pH 7.4 washing solution: 0.9% NaCl; 0.1% Tween 20;

substrate solution: substrate solution Enzymun (Boehringer Mannheim GmbH) contains 1.9 mM ABTS and 3.2 mM sodium perborate in phosphate-citrate buffer pH 4.4) containing 2 mg/ml vanillin.

Procedure

Coating

Microtitre plates (Maxisorp F96, Nunc Co.) are coated with streptavidin (Boehringer Mannheim GmbH) which is dissolved at a concentration of 5 $\mu$g/ml protein in the coating buffer. 100 $\mu$l of this solution is pipetted into each well of the microtitre plates. After incubating for 1 h at room temperature while shaking the solution is discarded and the plate is washed three times with washing solution.

Synthesis of Biotinylated Amphetamine-BSA Conjugate

Amphetamine-p-carboxybutyl-maleinimidoethylamide hydrochloride 9 and methamphetamine-p-carboxybutyl-maleinimidoethylamide acetate 18 are coupled to biotinylated BSA according to the processes described previously in example 3 to produce polyhaptens (capture matrix).

Reaction of the Antibodies with the Hastens

The antisera are diluted at least 1 to 10,000 with incubation buffer. In each case 50 $\mu$l of the diluted serum is added together with the hapten-BSA solutions to the wells and mixed. After incubating for 1 h at room temperature while shaking the solution is discarded and the plate is washed three times with washing solution.

Reaction with the Detection Conjugate

In order to detect the antibodies which are bound to the solid phase via the biotinylated hapten-BSA conjugate, a conjugate of horseradish peroxidase and rabbit antibodies against IgG from sheep is used. The detection conjugate is diluted with incubation buffer to 20 mU/ml peroxidase activity and this solution is distributed among the wells (100 $\mu$l/well). Incubation (60 minutes) and washing are carried out as described above.

Substrate Reaction

Each of the wells is filled with 100 $\mu$l substrate solution and incubated while shaking until the colour development in the negative controls appeared subjectively to be adequate. Afterwards the absorbance of all wells was determined as a differential measurement at the wavelengths 405/492 nm.

Example 5

Detection of anti-(meth)amphetamine antibodies

Example 4 is repeated except that a solid phase-bound BSA-hapten conjugate is used instead of the biotinylated BSA-hapten conjugate.

Example 6

Detection of amphetamines

Streptavidin-coated microtitre plates are prepared as described above in example 4 and biotinylated conjugates of anti-amphetamine antibodies are prepared according to example 3.

Detection Conjugate

A conjugate of horseradish peroxidase and amphetamine or methamphetamine which is obtained by reacting the activated conjugates 9 or 18 with horseradish peroxidase is used to detect haptens which are bound to the solid phase via the antibody-biotin conjugate in the competitive method used.

Reaction of the Antibodies with the Hastens

A dilution series of amphetamine and methamphetamine is prepared in incubation buffer. The series contains a total of 10 different concentrations in dilution steps of 1:3 starting with a maximum concentration of (1 $\mu$g/ml). Incubation buffer without hapten is used as a comparison.

50 $\mu$l each of amphetamine solution, detection conjugate (20 mU/ml peroxidase activity) and biotinylated antibody solution are distributed among the wells. After incubation for 1 h at room temperature while shaking the solution is removed and the plate is washed three times with washing solution.

Substrate Reaction

All wells are filled with 100 $\mu$l substrate solution and incubated while shaking until the colour development in the samples without hapten appears subjectively to be adequate. Then the absorbance of all wells is determined as a differential measurement at the wavelengths 405/492 nm.

LITERATURE

1. L. T. Cheng, FEBS Letters 36 (1973), 339–42
2. S. Inayama, Chem. Pharm. Bull. 28 (1977), 2779–82
3. P. A. Mason, J. Immunoassay 4 (1988), 83–98
4. S. A. Eremin, Ther. Drug. Mon. 10 (1988), 327–32
5. U.S. Pat. No. 3,690,834, Sep. 12, 1972

6. U.S. Pat. No. 4,067,774, Jan. 10, 1978
7. EP-0 311 383, Oct. 6, 1988
8. EP-0 399 184, Apr. 3, 1990
9. EP-0 359 063, Sep. 1, 1989
10. G. Cavallini, Il Farmaco 11 (1956), 805–10
11. D. Colbert, Clin. Chem. 31 (1985), 1193–95
12. G. Gallacher, Ther. Drug Mon. 11 (1989), 607–11
13. K. Aoki, Forensic Sci. Int. 44 (1990), 245–55
14. K. Terazawa, J. Immunoassay 12 (1991), 277–291
15. EP-0 279 213, Jan. 22, 1988
16. U.S. Pat. No. 401,646, Apr. 5, 1977
17. U.S. Pat. No. 3,878,187, Apr. 15, 1975
18. EP-0 375 422, Dec. 21, 1989
19. U.S. Pat. No. 4,041,076, Aug. 9, 1977
20. U.S. Pat. No. 4,329,281, May 11, 1982
21. EP-0 386 644, Mar. 2, 1990
22. T. Niwaguchi, J. Forensic Sci. 27 (1982), 592–97
23. T. Usagawa, J. Immunol. Meth. 119 (1989), 111–15
24. WO90/15798, Jun. 16, 1990

We claim:

1. An activated amphetamine derivative having the structural formula

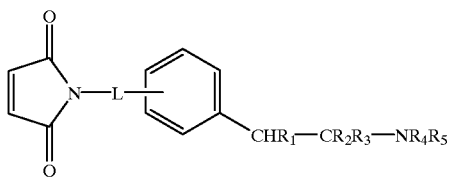

in which $R_1$ is H or OH, $R_2$, $R_3$, $R_4$, and $R_5$ are independently of one another H, $CH_3$ or $C_2H_5$, and L is a linker of formula $(-CH_2)_o-NH-C(O)-)_p-(CH_2)_q-X-$, in which o is 2 to 6, p is 1 or 2, q is 2 to 10 and X is selected from the group consisting of O, NH and a bond, or a salt of said activated amphetamine derivative.

2. The activated amphetamine derivative of claim 1, wherein $R_5$ is H.

3. The activated amphetamine derivative of claim 1, wherein the linker is in the p-position relative to the ethylamine side chain.

4. The activated amphetamine derivative of claim 1, wherein p is 1 and X is a bond.

5. The activated amphetamine derivative of claim 1, wherein o is 2 and q is 4.

6. The activated amphetamine derivative of claim 1, wherein $R_1$, $R_3$ and $R_5$ are H, $R_2$ is $CH_3$ and $R_4$ is H or $CH_3$.

7. A conjugate, comprising at least one amphetamine group and a conjugation partner P, obtained by reacting the maleinimide group of an activated amphetamine derivative of claim 1 with an SH group of the conjugation partner, wherein said conjugate has the structural formula

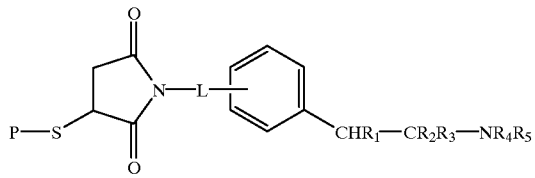

8. A conjugate, having the structural formula

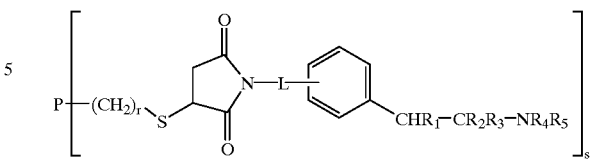

in which P is a conjugation partner, $R_1$ to $R_5$ are defined as in claim 1, r is 0 to 10, s is 1 to 40 and L is defined as in claim 1, or a salt of said conjugate.

9. The conjugate of claim 8, wherein p is 1.

10. The conjugate of claim 8, wherein o is 2 and q is 4.

11. The conjugate of claim 8, wherein $R_1$, $R_3$ and $R_5$ are H, $R_2$ is $CH_3$ and $R_4$ is H or $CH_3$.

12. The conjugate of claim 8, wherein P is selected from the group consisting of a immunoglobulin, a enzyme, a dye, and a metal label.

13. The conjugate of claim 8, wherein said conjugate is bound to a solid phase or has a group which is capable of binding to a solid phase.

14. A process for the production of an activated amphetamine derivative of claim 1, wherein a linker is introduced on the aromatic ring of the amphetamine in a one-step or multiple-step synthesis wherein the amino group of the amphetamine side chain is protected during the synthesis, the derivative that is formed is reacted with maleinimide alkylamine, the protective group is removed and the activated amphetamine derivative is isolated.

15. A process for the production of a conjugate of claim 7, wherein an activated amphetamine derivative of claim 1 is reacted together with a reagent $P-(-(CH_2)_r-SH)_s$ in which P, r and s are defined as claimed in claim 8 under such conditions that an addition of the SH groups to the double bond in the maleinimide functionality occurs and the reaction product is isolated.

16. A reagent kit comprising an activated amphetamine derivative of claim 1.

17. The conjugate of claim 12, wherein the dye is a fluorescent dye.

18. A reagent kit comprising the conjugate of claim 7.

19. A reagent kit comprising an activated amphetamine derivative characterized by the structural formula

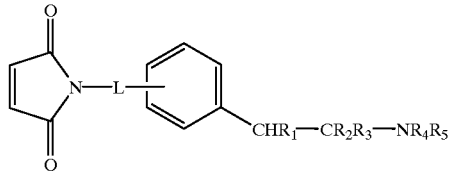

in which $R_1$ is H or OH, $R_2$, $R_3$, $R_4$ and $R_5$ are independently of one another H, $CH_3$ or $C_2H_5$, and L is a linker as defined in claim 1 and a conjugate of claim 7.

20. A pharmaceutical composition comprising the conjugate of claim 7 and a pharmaceutically acceptable carrier.

21. A method for producing antibodies against an amphetamine or a derivative thereof comprising inoculating a subject with the pharmaceutical composition of claim 20.

22. A method for determining the presence of amphetamines or derivatives thereof in a sample comprising contacting said sample with the conjugate of claim 7 and determining presence of said amphetamines.

* * * * *